United States Patent [19]

Brothers

[11] Patent Number: 4,958,498
[45] Date of Patent: Sep. 25, 1990

[54] CRYOGENIC STORAGE DEVICE

[75] Inventor: James L. Brothers, Warren, Mich.

[73] Assignee: Custom Biogenic Systems, Warren, Mich.

[21] Appl. No.: 468,851

[22] Filed: Jan. 23, 1990

[51] Int. Cl.$^5$ ............................................. F25B 19/00
[52] U.S. Cl. ....................................... 62/51.1; 62/78; 62/457.9
[58] Field of Search ...................... 62/457.9, 78, 51.1

[56] References Cited

U.S. PATENT DOCUMENTS

| | | | |
|---|---|---|---|
| 3,411,318 | 11/1968 | Puckett | 62/457.9 |
| 3,633,381 | 1/1972 | Haaf et al. | 62/457.9 |
| 3,952,536 | 4/1976 | Faust et al. | 62/457.9 |
| 4,006,606 | 2/1977 | Underdue | 62/457.9 |
| 4,543,798 | 10/1985 | Page | 62/457.9 |
| 4,580,411 | 4/1986 | Orfitelli | 62/51.1 |
| 4,846,257 | 7/1989 | Wallace et al. | 62/457.9 |

*Primary Examiner*—Ronald C. Capossela
*Attorney, Agent, or Firm*—Gifford, Groh, Sprinkle, Patmore and Anderson

[57] ABSTRACT

A cryogenic storage device is disclosed having a lower housing part adapted to contain a cryogenic storage tank. An upper housing part is detachably secured to the upper end of the lower housing part so that the upper housing part covers and overlies the cryogenic storage tank. A lid in the upper housing part provides access to the top of the cryogenic storage tank. An electronic circuit arrangement which controls both a fill solenoid for the storage tank as well as an exhaust fan is contained wholly within the upper housing part. Consequently, upon detachment of a single fluid connection between the valve means and the upper housing part and a fill line from the cryogenic storage tank, the upper housing part can be detached from the lower housing part and the storage tank for shipment and/or servicing.

5 Claims, 1 Drawing Sheet

CRYOGENIC STORAGE DEVICE

BACKGROUND OF THE INVENTION

I. Field of the Invention

The present invention relates to a cryogenic storage device.

II. Description of the Prior Art

There are a number of previously known cryogenic storage devices for storing sperm specimens, tissue cultures and the like. The previously known storage units typically comprise a housing in which a cryogenic storage tank is contained. Plumbing is attached directly to the housing for connecting the fill line of the cryogenic storage tank to an external source of coolant, typically liquid nitrogen. Thus, whenever the level of the nitrogen in the storage tank falls below a predetermined amount, the circuitry opens the valve between the external coolant source and the fill line of the storage tank thus filling the storage tank in the desired fashion.

These previously known storage tanks, however, have suffered from a number of disadvantages. One disadvantage of these previously known storage tanks is that such storage tanks are very difficult to repair and maintain. For example, in the event of failure of one of the components of the storage tank, for example the electronic circuitry or the plumbing components, it is necessary to ship the entire housing, and oftentimes the crygenic storage tank, back to the factory. This is very expensive since such housings are typically three or four feet tall, several feet wide and several feet deep.

A still further disadvantage of these previously known cryogenic storage devices is that, when the lid of the storage tank is opened, nitrogen vapors create a fog at the top of the storage tank. These nitrogen vapors obscure the vision of the operator when inserting specimens into or removing specimens from the cryogenic storage tank.

SUMMARY OF THE PRESENT INVENTION

The present invention provides a cryogenic storage device which overcomes all of the above mentioned disadvantages of the previously known device.

In brief, the storage device of the present invention comprises a housing having an upper housing part and a lower housing part. The lower housing part has an interior chamber dimensioned to receive a standard cryogenic storage tank so that the top of the cryogenic storage tank is positioned adjacent the top of the lower housing part.

The upper housing part is detachably secured to the lower housing part by any conventional means, such as loop and pile fasteners. Furthermore, the valve means for fluidly connecting an external source of coolant to the fill line of the storage tank, as well as the circuit means for controlling actuation of the valve means, are wholly contained within and secured to the upper housing part. Consequently, all of the serviceable components of the cryogenic storage device, i.e. the electronic and valve components, can be detached from both the lower housing part as well as the storage tank by simply fluidly disconnecting the upper housing part from the storage tank. Thereafter, the upper housing part along can be returned to the factory for repair and/or replacement.

In addition, the present invention includes an exhaust fan which is also mounted within the upper housing part. The upper housing part includes a lid which, when open, closes a switch and activates the fan. Activation of the fan exhausts the nitrogen vapors in the desired fashion.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 2:
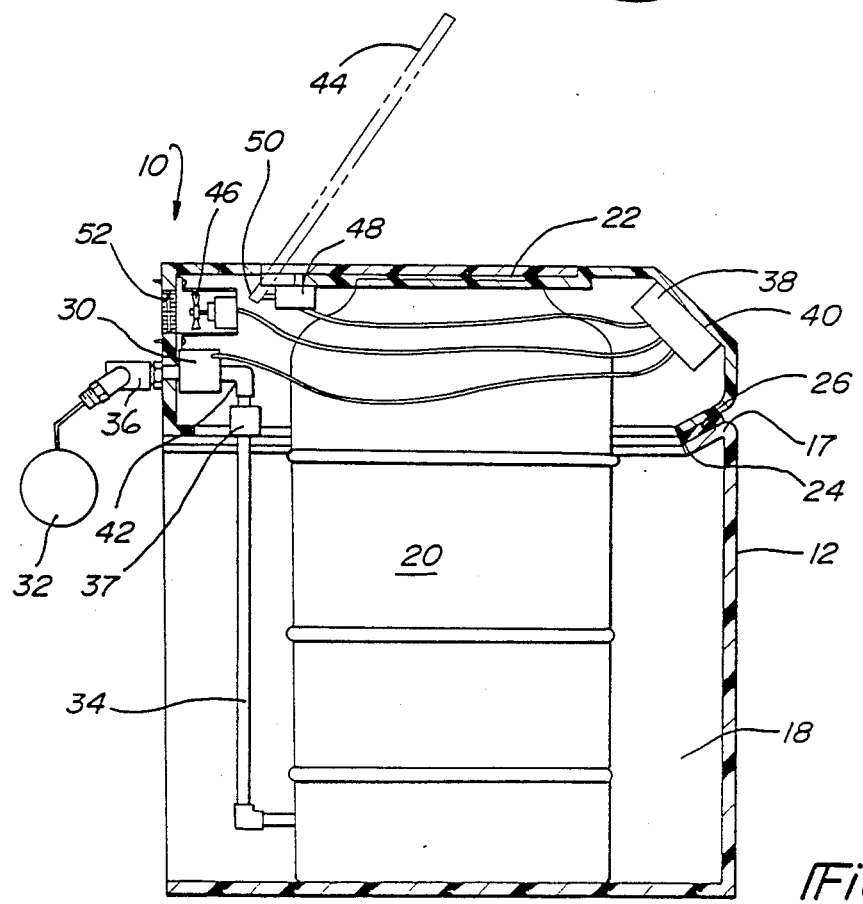
FIG. 2 is a sectional view taken substantially along line 2—2 in FIG. 1.

With reference to the drawing, a preferred embodiment of the cryogenic storage device 10 of the present invention is thereshown and comprises a housing 11 having a lower housing part 12 and an upper housing part 14. As best shown in FIG. 2, the lower housing part 12 is open at its top 17 and defines an interior chamber 18.

The lower housing part 12 is dimensioned to receive a standard cryogenic storage tank 20 within its interior so that a top 22 of the storage tank 20 is positioned adjacent the top 17 of the lower housing part 12. Consequently, the storage tank 20 protrudes upwardly from the top 17 of the lower housing part 12 by a small distance.

As best shown in FIG. 2, the upper housing part 14 is open at its bottom 24 and is detachably secured to the lower housing part 12 so that the upper housing part 14 covers and overlies not only the top of the lower housing part 12, but also the top 22 of the storage tank 20. Any conventional means, such as a loop and pile fastener 26, can be used to detachably secure the housing parts 12 and 14 together.

Referring now to FIG. 2, a solenoid operated valve 30 is secured to and contained within the upper housing part 14. This solenoid valve 30 is adapted for connection between an external coolant source 32, such as a source of liquid nitrogen, and a fill line 34 on the storage tank 20. A standard fluid coupling 37 is used to connect the solenoid valve 30 to the fill line 34.

Figure 1:
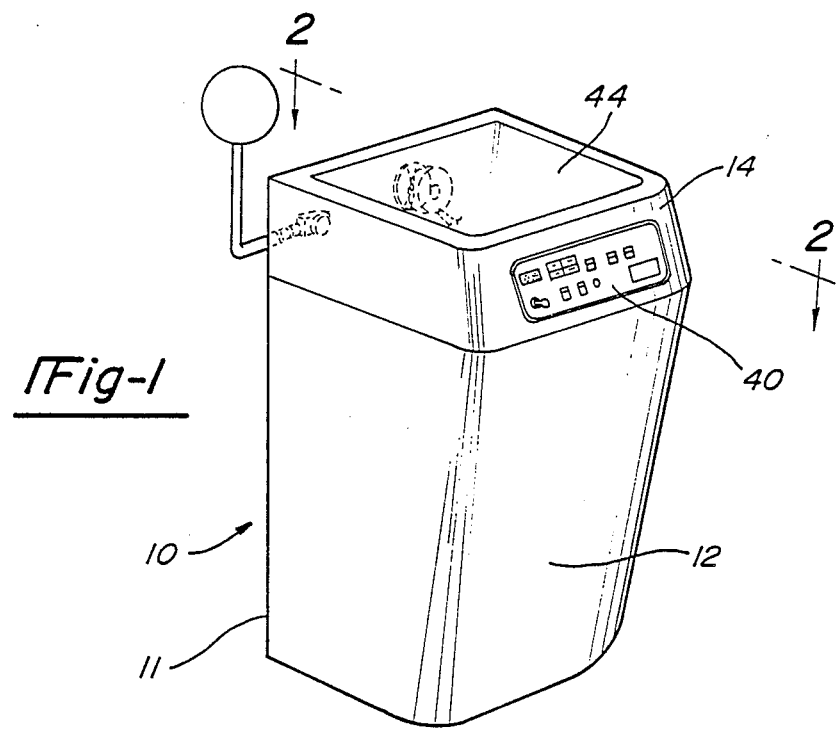
FIG. 1 is a perspective view illustrating a preferred embodiment of the present invention.

Referring now to FIGS. 1 and 2, an electronic circuit 38 having a front control panel 40 is also secured to and contained within the upper housing part 14. This electronic control circuit 38 is electronically connected with the solenoid valve 30 and opens the solenoid valve 30 to fill the storage tank 20 from the coolant source 32 whenever the level of coolant within the storage tank 20 falls below preset values. A sensor 42 adjacent the solenoid valve 30 provides an electronic signal to the ciruict 38 indicative of the level of liquid in the storage tank 20.

Referring again to FIGS. 1 and 2, a lid 44 is pivotally connected to the upper housing part 14 and is movable between an open position, illustrated in FIG. 2, and a closed position, illustrated in FIG. 1. In its closed position (FIG. 1) the lid 44 covers the top of the storage tank 20. Conversely, when the lip 44 is in its open position (FIG. 2) the top 22 of the storage tank 20 is accessible through the top of the upper housing part 14 for the insertion or removal of specimens into or from the storage tank 20.

Referring now particularly to FIG. 2, an exhaust fan 46 is secured to and contained within the upper housing part 14. A switch 48 cooperates with a portion of the lid portion 50 so that, when the lid 44 is moved to its open position, the lid portion 50 engages the switch 48 which activates the extaust fan 46. Once the exhaust fan 46 is activated, it exhausts nitrogen vapors out through the vent openings 52.

A primary advantage of the cryogenic storage device of the present invention is that, upon disconnection of the single fluid coupling 37 between the housing parts 12 and 14, and the fluid coupling 36 between the external nitrogen source 32 and the storage device 10, the entire upper housing part 14 can be detached from the lower housing part 12 and storage tank 20. The upper housing part 14, together with its attached electronic circuit 38, fan 46 and valve means 30 can then be easily shipped as required for maintenance and/or repair.

From the foregoing, it can be seen that the present invention provides a cryogenic storage device which overcomes all of the previously discussed disadvantages of the previously known storage devices. Having described my invention, however, many modifications thereto will become apparent to those skilled in the art to which it pertains without deviation from the spirit of the invention as defined by the scope of the appended claims.

I claim:

1. A cryogenic storage device comprising:
   a housing having a lower part and an upper part, said lower housing part having an interior chamber and an open upper end,
   a cryogenic storage tank insertable into said interior chamber of said lower housing part so that an upper end of said storage tank is adjacent said upper end of said lower housing part and adjacent said upper housing part said storage tank having a fill line,
   means for detachably securing said housing parts together so that said upper housing part overlies said storage tank,
   valve means contained in said upper housing part, said valve means adapted to be fluidly connected between an external source of coolant and said storage tank fill line,
   circuit means for controlling actuation of said valve means, said circuit means being contained within said upper housing part so that, upon detachment of said valve means from said fill line, said upper housing part is detachable from said lower housing part and said storage tank.

2. The invention as defined in claim 1 wherein said upper housing part further comprises a lid movable between an open and a closed position wherein, in said open position, said lip exposed the top of said storage tank while in said closed position said lid covers the top of said storage tank.

3. The invention as defined in claim 2 and comprising a fan attached to said upper housing part and means for automatically activating said fan when said lid is moved to said open position.

4. The invention as defined in claim 3 wherein said activating means comprises a switch attached to said upper housing part which cooperates with a portion of said lid.

5. The invention as defined in claim 1 wherein said detachable securing means comprises a loop and pile fastener.

* * * * *